US011059017B2

(12) United States Patent
Buchner, Sr. et al.

(10) Patent No.: US 11,059,017 B2
(45) Date of Patent: Jul. 13, 2021

(54) HALOGEN SELECTIVE DETECTION GAS CHROMATOGRAPHY FOR THE ON-LINE ANALYSIS AND CONTROL OF SELECTIVE OXIDATION CHEMICAL PRODUCTION PROCESSES

(71) Applicant: MultiPhase Solutions, Inc., Butler, PA (US)

(72) Inventors: James D. Buchner, Sr., Allison Park, PA (US); James D. Buchner, Jr., Pittsburgh, PA (US)

(73) Assignee: MultiPhase Solutions, Inc., Butler, PA (US)

( * ) Notice: Subject to any disclaimer, the term of this patent is extended or adjusted under 35 U.S.C. 154(b) by 19 days.

(21) Appl. No.: 16/131,620

(22) Filed: Sep. 14, 2018

(65) Prior Publication Data

US 2019/0083951 A1    Mar. 21, 2019

Related U.S. Application Data

(60) Provisional application No. 62/559,172, filed on Sep. 15, 2017.

(51) Int. Cl.
*B01J 19/00*    (2006.01)
*C07D 301/10*    (2006.01)
(Continued)

(52) U.S. Cl.
CPC ........ *B01J 19/0033* (2013.01); *B01D 53/025* (2013.01); *B01J 19/0006* (2013.01);
(Continued)

(58) Field of Classification Search
CPC ...... C07D 301/10; Y02P 20/52; Y02P 20/142; B01J 19/033; B01J 19/0006;
(Continued)

(56) References Cited

U.S. PATENT DOCUMENTS 2,550,498 A    4/1951 Rice
2,795,716 A    6/1957 Roberts
(Continued)

FOREIGN PATENT DOCUMENTS

EP    0352850 A1    1/1990
WO    9710030 A1    3/1997

OTHER PUBLICATIONS

O I Analytical, "Model 5360 Halogen Specific Detector (XSD) Operator's Manual", 2002, pp. 1-53.
(Continued)

*Primary Examiner* — Lore R Jarrett
(74) *Attorney, Agent, or Firm* — The Webb Law Firm

(57) ABSTRACT

A method for process monitoring and control of a chemical reactor in which a chemical reaction utilizing a halogenated selectivity modifier is performed includes: measuring a level of halogenated components in an inlet stream of a reactor inlet; measuring a level of halogenated components in an outlet stream of a reactor outlet; based on the level of halogenated components at the inlet stream and the outlet stream, determining a process performance indicator associated with a halogenated component; and adjusting an amount of halogenated selectivity modifier added to the reactor based on the process performance indicator.

25 Claims, 4 Drawing Sheets

(51) Int. Cl.
*B01D 53/02* (2006.01)
*G01N 30/70* (2006.01)
*G01N 30/72* (2006.01)
*G01N 30/62* (2006.01)
*G01N 30/88* (2006.01)
*G01N 30/00* (2006.01)
*G01N 30/02* (2006.01)
*G01N 30/86* (2006.01)

(52) U.S. Cl.
CPC .......... *C07D 301/10* (2013.01); *G01N 30/62* (2013.01); *G01N 30/70* (2013.01); *G01N 30/7206* (2013.01); *G01N 30/88* (2013.01); *B01J 2219/00051* (2013.01); *B01J 2219/00164* (2013.01); *B01J 2219/00182* (2013.01); *B01J 2219/00186* (2013.01); *B01J 2219/00198* (2013.01); *B01J 2219/00202* (2013.01); *G01N 30/8665* (2013.01); *G01N 2030/025* (2013.01); *G01N 2030/77* (2013.01); *G01N 2030/8804* (2013.01); *G01N 2030/8868* (2013.01)

(58) Field of Classification Search
CPC .... B01J 2219/00182; B01J 2219/00198; B01J 2219/00051; B01J 2219/00164; B01J 2219/00186; B01J 2219/00202; G01N 2030/025; G01N 2030/77; G01N 30/88; G01N 30/62; G01N 30/7206; G01N 30/70; G01N 2030/8804; G01N 30/8665; G01N 2030/8868; B01D 53/025
See application file for complete search history.

(56) References Cited

U.S. PATENT DOCUMENTS

| | | |
|---|---|---|
| 4,874,879 A | 10/1989 | Lauritzen et al. |
| 5,019,517 A | 5/1991 | Coulson |
| 5,155,242 A | 10/1992 | Shankar et al. |
| 5,525,197 A | 6/1996 | Coulson |
| 6,372,925 B1 | 4/2002 | Evans et al. |
| 6,717,001 B2 | 4/2004 | Evans et al. |
| 7,142,974 B2 | 11/2006 | Sugita et al. |
| 7,193,094 B2 | 3/2007 | Chipman et al. |
| 7,657,331 B2 | 2/2010 | Chipman et al. |
| 7,657,332 B2 | 2/2010 | Chipman et al. |
| 8,487,123 B2 | 7/2013 | Rizkalla et al. |
| 8,530,682 B2 | 9/2013 | Sachs et al. |
| 8,546,592 B2 | 10/2013 | Evans et al. |
| 8,624,045 B2 | 1/2014 | Sachs et al. |
| 8,742,146 B2 | 6/2014 | Hess et al. |
| 8,742,147 B2 | 6/2014 | Evans et al. |
| 8,859,792 B2 | 10/2014 | Evans et al. |
| 9,067,902 B2 | 6/2015 | Padia et al. |
| 9,174,928 B2 | 11/2015 | Evans et al. |
| 9,221,774 B2 | 12/2015 | Al-Ahmadi et al. |
| 9,221,776 B2 | 12/2015 | Schmitz et al. |
| 9,346,774 B2 | 5/2016 | Matusz et al. |
| 2004/0181088 A1 | 9/2004 | Watanabe et al. |
| 2006/0102519 A1* | 5/2006 | Tonkovich ............... C11C 3/126 208/107 |
| 2007/0129557 A1* | 6/2007 | Chipman ............... C07D 301/10 549/535 |
| 2007/0142974 A1 | 6/2007 | Chipman et al. |
| 2009/0281339 A1* | 11/2009 | Matusz ............... C07D 301/10 549/523 |
| 2010/0267972 A1* | 10/2010 | Zhang ............... C07D 301/10 549/518 |
| 2011/0160470 A1* | 6/2011 | Henstock ............... C07D 301/36 549/534 |
| 2013/0096330 A1 | 4/2013 | Al-Ahmadi et al. |
| 2013/0288379 A1 | 10/2013 | Habenschuss et al. |

OTHER PUBLICATIONS

Farwell et al., "Current Status of Prominent Selective Gas Chromatographic Detectors: A Critical Assessment," Journal of Chromatographic Science, 1981, pp. 358-376, vol. 19, Department of Chemistry, University of Idaho, Moscow, Idaho.
Grant et al., "Alkali-Metal Promoters and Catalysis: A Single-Crystal Investigation of Ethylene Epoxidation on Cs-Doped Ag(111)", Langmuir, 1985, pp. 29-33, vol. 1, Department of Chemistry at Queen Mary, University of London.
Kay et al., "A laboratory investigation of a multigas monitor for anaesthesia (EMMA)," Anaesthesia, 1982, pp. 446-450, vol. 37.
McQuarrie et al., "Physical Chemistry, A Molecular Approach", 1997, pp. 941,1063-1066, and 1295, University Science Books.
Obersteiner et al., "An automated gas chromatography time-of-flight mass spectrometry instrument for the quantitative analysis of halocarbons in air," Atmospheric Measurement Techniques, 2016, pp. 179-194, vol. 9.
Santen, "Selective Oxidations: Epoxidation Catalysis Using Heterogeneous Catalysts", 1944, pp. 2244-2252, vol. 4, Organic Reactions.
Schouten et al., "Influence of reaction products on the selective oxidation of ethene", Chemical Engineering and Processing, 1996, pp. 102-120, vol. 35, Elsevier Science S.A.
Serafin et al., "Surface science and the silver-catalyzed epoxidation of ethylene: an industrial perspective", Journal of Moleculart Catalysis A: Chemical 131, 1998, pp. 157-168, Elsevier Science B.V.
Whitmore, "Adsorption and Catalysis", 2008 pp. 31-42, Sarup & Sons.

* cited by examiner

HALOGEN SELECTIVE DETECTION GAS CHROMATOGRAPHY FOR THE ON-LINE ANALYSIS AND CONTROL OF SELECTIVE OXIDATION CHEMICAL PRODUCTION PROCESSES

CROSS REFERENCE TO RELATED APPLICATIONS

This application claims priority to U.S. Provisional Application No. 62/559,172, filed Sep. 15, 2017, the disclosure of which is hereby incorporated in its entirety by reference.

BACKGROUND OF THE INVENTION

Field of the Invention

The present invention relates to a system and method for process monitoring and control of a chemical reactor in which a chemical reaction utilizing a halogenated selectivity modifier is performed.

Description of Related Art

Organohalide compounds, most generally C1-C8 chlorinated, brominated, or fluorinated hydrocarbons, are used as moderators to optimize the selectivity of oxidation reactions using alumina supported silver catalysts (U.S. Pat. Nos. 4,874,879, 5,155,242, 6,372,925 and others). The halide modifiers are generally added to the feedstock or recycle fluids. The native modifier compound generally reacts with other process gases to form halide compounds with a different chemical structure. The measured fluid phase concentrations of the various organohalides are important for control of the catalyst activity, and the selectivity to produce the desired product EO.

When organohalide compounds are used as modifiers, the ability of the various organohalides to modify catalyst properties varies with structure so that accurate measurement of the individual halide species present in the gas phase is important to reactor control. The ability to modify catalyst behavior can be expressed as a factor. The factors are generally empirically determined, but are thought to be a function of the number of heteroatoms in the molecule and the ability of the molecule to donate them (U.S. Pat. Nos. 7,193,094, 7,657,331). The sum of the products of each modifier species molar concentration multiplied by its modifying factor produces a key engineering control parameter often referred to as total effective modifier, in this case total effective halides (TEX where X=C, B or F depending on the halogen atom as Cl, Br, or F respectively). In the TEC case where X=Cl in the ethylene oxide (EO) process, four or five components are usually considered, namely, methyl chloride (MC), vinyl chloride (VC), ethyl chloride (EC), ethylene dichloride (EDC), and optionally allyl chloride (AC).

When the process is carried out with recycle gas, the various organohalide species presented to the reactor inlet is largely reflective of the hydrocarbon composition in the reactor, since it is these hydrocarbons which strip chlorine from the catalyst surface and lead to their formation. Each hydrocarbon species has a different ability to strip chloride from the catalyst and form an organochloride compound. This leads to another set of factors used to adjust the molar hydrocarbon concentrations to consider the chloride stripping effect of the reactor hydrocarbons (US Pat. No. 2007/0142974), and a sum of all hydrocarbon contributions (molar concentration multiplied by a stripping factor) as a term that we will call total effective hydrocarbons (TEH).

In various commercial means a chloride control factor (CCF or I-factor) is often calculated as a ratio of TEC/TEH. Shell patent (U.S. Pat. No. 7,142,974 A1; Process and Systems for the Epoxidation of an Olefin, [0010]) teaches that:

$$Q=TEC/TEH,$$

where TEC=total effective chlorides and TEH=total effective hydrocarbons.

Q represents a fundamental control parameter (or key performance indicator: KPI) in the Shell patent literature. In operating practice this ratio is commonly called "Ifactor" (Q=Ifactor=TEC/TEH). Q (Ifactor) is defined as the "ratio of the effective molar quantity of active species of the reaction modifier present in the feed to an effective molar quantity of hydrocarbons present in the feed" (U.S. Pat. No. 7,142,974 A1; Process and Systems for the Epoxidation of an Olefin, Abstract). This ratio is basically a balance point for the reaction modifier as a function of reactor temperature and other conditions. It represents the ratio of the total effective chlorides (TEC) being added to the catalyst and the chlorides being stripped away from the catalyst. This invention creates an alternative route to calculate "Q" where the halide being stripped from the catalyst is measured directly in the outlet stream rather than being calculated using external hydrocarbon data and associated assumptions.

As a catalyst ages, increases in reactor temperature are required to maintain optimized process conditions. Therefore, effective process control algorithms for modifier addition must consider the changes in reactor temperature.

When Q is optimized for highest catalyst selectivity, basic rules of thumb exist regarding the change in Q as a function of change in reactor temperature for ongoing control of the organohalide addition to maintain maximum selectivity performance.

Shell (U.S. Pat. No. 7,142,974 A1; Process and Systems for the Epoxidation of an Olefin, [0018]) relates changes in Q to changes in reactor temperature, T, through:

$$Q_2=Q_1+B(T_2-T_1)$$

where B=a constant factor, $T_1$=a first reactor temperature at a first time; $T_2$=a second reactor temperature at a second time, Q1=TEC/TEH at T1, Q2=TEC/TEH at T2.

Other automated methods for routine modifier control with changes in reactor temperature have been proposed. Schmitz et. al. (U.S. Pat. No. 9,221,776) proposes an exponential function for relating changes in modifier concentration (M) as a function of temperature (T) change using:

$$M_2=M_1(1+r)^{T2-T1}, \text{ where } r=\text{a constant factor.}$$

The expression does not explicitly recognize the removal of halides from the catalyst. M is defined as the total of concentration of all organochlorides in the feed. There is no correction of each individual organohalide species for modifier effectiveness taught. It is not known if this method is in routine practice.

In the absence of an automated algorithm for routine chloride control, the plant running high selectivity catalyst (HSC) must perform routine checks to verify whether the chloride level is still optimum. At some frequency, or based on shifting reactor performance, the plant changes chloride level "slightly" and observes the changes in selectivity. These small incremental changes may require increasing and decreasing TEC until a maximum selectivity level is identified (U.S. Pat. Nos. 2013/0096330 & 8,742,147 B2). Since the catalyst responds slowly to these incremental chloride changes, and numerous step changes may be required, these actions take away production time at an optimal organohalide level.

The magnitude of the step change is important to consider. It is well understood that high selectivity catalysts (HSC) tend to exhibit relatively steep curves of selectivity versus modifier concentration (U.S. Pat. Nos. 7,657,332 B2 & 9,221,774 B2; EP 0 352 850 A1). FIG. 3 in EP 0 352 850 A1 and FIG. 2 in U.S. Pat. No. 9,221,774 B2 show these relationships. It is estimated that a +/−5% change in TEC from that associated with the selectivity maximum can result in a selectivity drop of 0.5 mol %. This is a significant change in selectivity if the plant wishes to optimize EO production. At start of run (SOR) in the life of the catalyst TEC may be 2.0-3.0 ppm and 5% of this TEC is 0.10-0.15 ppm. The high level of dependence of selectivity to TEC is also taught in U.S. Pat. No. 8,859,792 B2 where it is recited that "practically, changes in chloride levels less than 0.2 ppm will have an impact on catalyst performance that cannot be measured precisely." U.S. Pat. No. 8,859,792 B2 concludes that reasonable step changes for the moderator is around 0.2 ppm using currently available process analytics. The current invention allows for analytically significant step changes as fine as 0.01 ppm. With improved "resolution" in step change a more precise location of modifier level corresponding with optimal selectivity can be established and maintained.

Methods for chloride control during plant startup after new catalyst charges, or after aged catalysts are brought back after a prolonged shut-in period have been described. Without reciting the detailed procedure, U.S. Pat. No. 9,346,774 B2 describes an "initial startup phase" where the catalyst is conditioned with organohalide modifier in the feed at a concentration between 2-10 ppm until there is an increase in VC of 0.1-0.5 ppm detected in the reactor outlet or the recycle gas loop. After VC increases in the "initial startup phase", chlorides are adjusted systematically through an "intermediate startup phase" concentration, and then finally to the "start-up adjustment phase" where an optimum value for EO selectivity is established.

U.S. Pat. No. 8,530,682 B2 describes a three-step process with step 1 initiating the epoxidation reaction, step 2 the addition of 0.05-2 ppm of the moderator, followed by a temperature increase to 240-250 C.

U.S. Pat. No. 8,487,123 B2 describes a two-step process in "conditioning" the HSC using organohalide moderator. After initiation of the process in the presence of the epoxidation catalyst without moderator, the moderator is added to the feed at a level of 0.2-2 ppm while temperature is increased and held for 50-350 hours. The moderator is then raised to between 0.5-5 ppm during the process of adjusting the reactor to a third production level temperature.

Many more startup procedures have been suggested as beneficial. All involve some stages of conditioning the catalyst with organohalide modifier at specified levels with variations in feed composition and temperature. Therefore, valid and consistent measurement data for these organohalide modifier compounds is important for startup and efficient routine operation of an EO plant using HSC. Gas chromatographic (GC) methods have been widely deployed in most EO plants to measure organohalide concentrations in reactor fluids.

GC is an analytical measurement tool where components present in a multicomponent mixture can be separated in space and time. The separation is based on differential partitioning of components between a mobile gas phase and a stationary phase. Typically, the two phases are confined within a tubular structure defining flow referred to as the column. The gas phase, referred to as the mobile phase, or the carrier gas, generally flows continuously through the column (unless components are being "held" for further separation). The stationary phase is either a thin film coating on the inside of the tubular column structure (open tubular column), or is coated onto a solid support which is packed in the column as a fine particulate. These latter column types are often referred to as packed or micro-packed columns. In the simplest case, the sample mixture is introduced onto the column in as small a volume as possible at the end where the carrier gas flow originates. The individual components present in the mixture migrate at various rates through the column inversely proportional to the time they spend in the mobile phase. Components having a high affinity for the stationary phase will spend less time in the mobile phase and therefore will be retained on the column for a longer period of time. The temperature of the column and the carrier gas flow rate through the column may be increased during the analysis to elute components more rapidly.

As components exit the column they pass to a detector whose function is to produce an output signal proportional to the input quantity of the component. The concentration profile of the component over the period of time that it elutes from the column most generally resembles a gaussian distribution and is referred to as a chromatography peak. The time corresponding to the maximum concentration (peak top) of this distribution is referred to as the retention time. Retention time is the key parameter in qualitative analysis (component identification) for individually separated components in GC. The area under this gaussian curve serves as the basis for quantitative analysis (component amount).

An important characteristic of a GC detector is the selectivity defined by the basic detector response mechanism. Mechanisms can vary substantially but are based on chemical and physical properties associated with specific compound classes. When a detector generates response for a specific class of compounds to the relative exclusion of others it is termed a specific or selective detector, for instance halogen selective or sulfur selective. Often the components of interest in a complex mixture have common chemical or physical properties that serve as a basis for the use of selective detectors.

Chromatography is an imperfect science given the large number of chemical molecules with different structure that exist and that can potentially co-elute to interfere with specific target compounds. Methods used to analyze complex mixtures by GC without selective detection are subject to false positive qualitative and quantitative data due to co-elution problems (chemical interferences). Analytical methods based on the use of selective or specific detectors benefit from the substantial reduction in the number of potential co-eluting compounds and therefore produce more reliable qualitative and quantitative analysis data.

The halide or halogen atom (element) has a 5 electron p-orbital configuration and as such will readily accept an electron to form X— and complete the p-orbital. This characteristic is the basis for several halogen selective response detectors. Other selective response for halogens can be based on spectral emission in a flame or plasma energy source.

Here we divide halogen selective detectors into several types depending on their response characteristics. Type 1 are defined as non-destructive selective detectors, such as electron capture detectors (ECD), which generate response based on the electron capture ability of the intact molecule. When electrons are captured by a molecular species the resulting negatively charged molecule has reduced mobility relative to free electrons flowing to a collector anode in the cell. The standing current of electrons produced inside the ECD detector cell is decreased as a portion are captured by intact molecules with high electron affinity that flow through the detector. Although the ECD detects halogenated species the selectivity can be low since many other compounds not containing halogen atoms also have high electron affinity. In addition, the ECD response is not proportional to the molar halogen content, but rather the electron affinity of the intact molecule.

We term halogen selective detectors as Type 2 when they are destructive and produce an output which is proportional to halogen content. Examples of these selective detectors are the dry electrolytic conductivity detector (DELCD; SRI Corporation), flame photometric detector (FPD), atomic emission detector (AED), hall electrolytic conductivity detector (ELCD), thermionic detector (TID; XSD, OI Corporation), and mass spectrometers (MS). Type 2 selective detectors are preferred due to their ability to assist qualitative location of halogenated components in the chromatography. Additionally, their response allows for a good estimate of concentration for "unknown" organohalides (non-targeted, i.e. those compounds for which standards have not been run or whose structure has not been elucidated).

Two Type 2 halogen selective detectors are particularly preferred in this invention for on-line process analysis based on hardware and operational simplicity. The particularly preferred type 2 selective detectors (DELCD; SRI Corporation and TID; XSD, OI Corporation) are based on the combustion of organohalide molecules to form small molecule or atomic level radical (odd electron species) combustion products which readily accept an electron at an activated cathode surface. The construction of these two detectors have common elements but are reported to have different response mechanisms. Additionally, they are reported to have been developed based upon different prior art (XSD based on the work of Rice (U.S. Pat. No. 2,550, 498) and Roberts (U.S. Pat. No. 2,795,716) while the DELCD based on the work of Coulson (U.S. Pat. Nos. 5,019,517 and 5,525,197)). We believe the devices act essentially in the same manner. The halogen:hydrocarbon selectivity ratio for these Type 2 particularly preferred selective detectors is around 40,000-60,000:1 for most of the targeted components used in the EO production process.

Currently all fixed location on-line GC analyzers that perform organochloride analysis in EO reactor inlet gas share much of the same top level design, that is, they use parallel chromatography with multiple columns (up to 9), multiple heart cuts, multiple flow restrictors to balance GC gas flows, isothermal column operation, and a carbon-based response flame ionization detector (FID). Heart cutting in analytical chromatography is a technique where target analytes are resolved from known interferences by diverting small time slices of the chromatographic profile containing the targets and other process matrix constituents onto other columns having different properties such as to further resolve the target compound from matrix interferences. This technique assumes that the pool of interferences in the process gas remains predictable over time. Since feedstock and reactor by-products may change over time this is at best a tenuous assumption.

Since an FID detects any compound containing CH, in this application it must be considered as nonselective since the bulk matrix for the process is hydrocarbon. Methods structured as such are inherently target component based, in the case of the EO process to measure five components, namely, methyl chloride (MC), vinyl chloride (VC), ethyl chloride (EC), allyl chloride (AC), and ethylene dichloride (EDC) which are the major components found in EO cycle gas. An FID will not detect any inorganic chlorides potentially present (i.e., HOCl, ClO, or $ClO_2$.

Prior and present art for the process analysis of organohalide components in selective oxidation process streams employs gas chromatography using a detector that has a carbon-based response. Since these streams are hydrocarbon based and contain a high number of hydrocarbon impurities, the analytical systems attempt to provide a high-quality analysis using multiple heart cutting methods. These instruments are inherently complex and often unreliable due to changes in the bulk matrix composition. Additionally, the data they provide are inherently target compound based and therefore do not consider other halogenated adducts present in the process fluids.

SUMMARY OF THE INVENTION

A method for process monitoring and control of a chemical reactor in which a chemical reaction utilizing a halogenated selectivity modifier is performed includes: measuring a level of halogenated components in an inlet stream of a reactor inlet; measuring a level of halogenated components in an outlet stream of a reactor outlet; based on the level of halogenated components at the inlet stream and the outlet stream, determining a process performance indicator associated with a halogenated component; and adjusting an amount of halogenated selectivity modifier added to the reactor, an amount of reactor feedstock, a flow rate, and/or a reactor temperature, based on the process performance indicator.

A system for process control of a chemical reactor in which a chemical reaction utilizing a halogenated selectivity modifier is performed includes: a chemical reactor in which a chemical reaction occurs which utilizes a halogenated selectivity modifier, wherein the chemical reactor includes: an inlet including an inlet stream including reactants and a halogenated component; and an outlet comprising an outlet stream including reactants, products, and a halogenated component; a halogen-selective detector in fluid communication with the inlet stream and the outlet stream and configured to measure a level of halogenated components in the inlet stream and the outlet stream; an analyzer configured to determine a process performance indicator associated with a halogenated component based on a level of halogenated components in the inlet stream and outlet stream; and a modifier input configured to adjust an amount of halogenated selectivity modifier added to the chemical reactor based on the process performance indicator.

A method for process monitoring and control of a chemical reactor in which a chemical reaction utilizing a halogenated selectivity modifier is performed includes: providing an inlet or outlet reactor sample stream; providing a gas chromatograph configured with a halogen selective detector in fluid communication with the reactor inlet or outlet stream; and analyzing halogenated catalyst modifier compounds in the reactor inlet or outlet streams to monitor or control modifier addition rates.

These and other features and characteristics of the present invention, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and the claims, the singular form of "a," "an," and "the" include plural referents unless the context clearly dictates otherwise.

DESCRIPTION OF THE INVENTION

Figure 1:
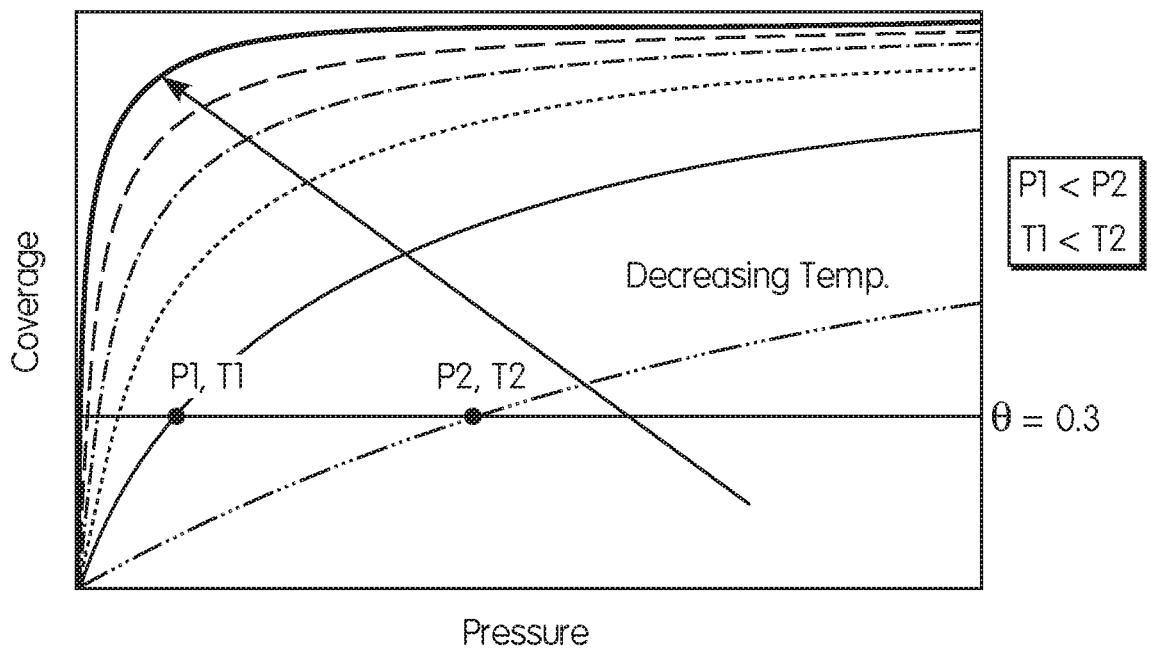
FIG. 1 shows a series of adsorption isotherms (each curve represents coverage (Θ) as a function of partial pressure at a fixed temperature). The points P1,T1 and P2,T2 represent constant coverage (Θ=0.3) intersects of T1 and T2 isotherms where T1<T2 and P1<P2. This example illustrates a method based on adsorption theory where catalyst surface modification required for optimal catalyst selectivity can be predicted as reactor temperatures are adjusted during the lifetime of the catalyst.

A method for precise and robust measurement of ppb-ppm levels of halogenated reaction modifier components for a catalyst surface is described. This method utilizes gas chromatography (GC) with a simplified chromatographic train, a halogen selective detector, an internal reference component for drift correction, and automated introduction of standards for calibration. The method produces complete halide (halogen containing component) measurement data in both reactor inlet and outlet streams for production processes, where an organohalide (organic halogen containing component) modifier is added at low levels to tailor catalyst properties. This design avoids complex chromatographic trains, provides sufficient detector specificity to minimize interferences present in most process gas matrices with component detection limits 10-100× better than traditional methods. Use of this method with extended engineering calculations significantly improves the precision and accuracy for reactor control.

In addition to improved analytical data, the method also leads to additional key performance indicators (KPI). The use of halogen selective detection coupled with the proper chromatographic conditions creates a "survey method" where all halogenated components, organic and inorganic, can be located within the process stream chromatography. As used herein, the term halogenated or halide component refers to any chemical species containing a halogen atom. This allows the method to compile a complete and accurate assessment of all halide components, and the generation of quantitative data to produce a chloride mass balance from reactor inlet and outlet sample analyses. The ability to express halide changes across the reactor directly through direct measurement data, rather than through inference, leads to unique KPI. These KPI can be in the form of a delta (differential) indicator or a thermodynamic (equilibrium) indicator.

A second type of KPI arises from the identification and quantification of all halide components and the opportunity to identify halide marker compounds for optimizing process conditions.

Optionally, with appropriate GC class separation coupled with a backflush step to the halogen selective detector a total halogen measurement (all species) can be made very rapidly on inlet or outlet reactor streams.

The present invention of novel process analytical chemistry methods is used to support the measurement and calculation of key parameters for proper process control. Feedback control of concentrations of reactants and modifiers using process analytics is a very important consideration in selectively oxidizing hydrocarbons using heterogeneous catalysis. The catalyst comprises a solid state and the reactants and products are fluids which are analyzed using this method. The selective oxidation of hydrocarbons leads to products and important intermediates for the petrochemical industry (ie. ethylene oxide (EO)).

The selectivity of these various processes to produce a desired product is often achieved using heterogeneous catalysis, a process where the activation energy for product formation is lowered (compared with that of competing processes) due to specific chemical interactions and reactions at a tailored catalyst surface. Improvements in selectivity can often be achieved using catalyst modifier agents. Organohalide compounds are an important type of selectivity modifier added to improve yield of the desired product for many of these reactions. Organohalide compounds can be abbreviated R—X where the halogen portion X=fluorine (F), chlorine (Cl), bromine (Br) or iodine (I) and R=any hydrocarbon substituent. These modifier components act through various mechanisms, including electronic modification of the catalyst surface characteristics, adjustment of the available surface area of the catalyst, and participation in transition state thermodynamics.

We describe the invention herein using the example of the selective oxidation of ethylene to form ethylene oxide (EO), but the methods are equally applicable for other selective oxidation reactions where halogenated compounds are used as catalyst modifiers. The EO ($C_2H_4O$) process commonly uses a silver catalyst activated by various alkali metals and other promoter systems generally supported on alumina. A mixture of ethylene ($C_2H_4$) and oxygen ($O_2$) are passed over a fixed bed of catalyst maintained at a sufficiently high reaction temperature. Since the ethylene conversion rate is low, the process is re-cycle gas based. The reactor effluent is passed through a scrubber where EO is removed, and a $CO_2$ removal unit, with the bulk of the remaining gases recycled. The new feed gas composition for the reactor is fortified with additional reactants and modifiers based on analyzer measurements.

The desired reaction (1) produces the cyclic ether EO, while the main competing reactions (2) and (4) produce $CO_2$. Reaction (3) is a minor side reaction producing the aldehyde. Reaction (4) is the result of EO oxidation at the surface of the catalyst before it becomes gas phase. Certain alkali metal promoters and organohalide modifiers suppress reactions (2) and (4).

$$C_2H_4 + \tfrac{1}{2}O_2 \rightarrow C_2H_4O \text{ (EO formation)} \quad 1)$$

$$C_2H_4 + 3O_2 \rightarrow 2CO_2 + 2H_2O \text{ (combustion of ethylene)} \quad 2)$$

$$C_2H_4 + \tfrac{1}{2}O_2 \rightarrow C_2H_4O \text{ (acetaldehyde)} \quad 3)$$

$$C_2H_4O + 2\tfrac{1}{2}O_2 \rightarrow 2CO_2 + 2H_2O \text{ (combustion of EO)} \quad 4)$$

Currently there are several different variants of catalyst product based on the promoter systems and the amount of silver. These catalyst products have a range of selectivity for EO production as well as other process and financial considerations. All catalysts used commercially for EO production use organohalide modifiers to improve performance High selectivity catalysts (HSC) generally have the greatest requirement for precise measurement and control of the organohalides. Reliable analytical measurements for halide components in the ppb-low ppm range are important to maintaining optimum process conditions.

With this invention we make improvements in the identification and measurement of targeted and non-targeted organohalide species, including the native addition modifier and halide containing reaction products, both organic and inorganic, using GC with halogen specific detection. Furthermore, through these means the comprehensive fate of the gas phase halogen atoms can be mapped and this information used to enhance process control and understanding for both reactor startup and routine process control purposes.

The reactor fluid chemical measurements, and the methods for reactor control that result from those measurements, are bounded by process analytic limitations. This invention uses gas chromatography with halogen selective detectors to generate a survey method where all halogenated components can be measured without significant chemical interference on both reactor input and reactor output streams. As used herein, "significant" chemical interference may be considered a chemical interference of more than 50 ppb. A chemical interference is defined herein as any other bulk matrix constituent which co-elutes chromatographically with a component to be measured where there is no or inadequate detector selectivity to allow differentiation. In addition to providing a simpler hardware and method structure with reduction in chemical interference, this invention also creates unique methods for reactor organohalide control using novel key performance indicators (KPI).

The present invention uses gas chromatography to separate components of interest from bulk matrix interferences in space and time. Additionally, a halogen selective detector is used to avoid interferences from other bulk matrix major component or ppb-ppm level impurities and byproducts. The selectivity of the particularly preferred detectors (Type 2) is high, around 60,000:1.

While halogen selective detectors have excellent sensitivity and specificity they often lack the long-term stability required for routine process measurements over time. To address this limitation, the current method invention incorporates a drift correction component which is introduced into the chromatographic flow stream separately from the sample to be measured, periodically, or with each sample. Sample related halogenated components are quantified relative to the drift correction component response. Introduction of the reference component may be made as a separate plug injection through the column, or directly into the detector, the result in both cases is to produce a proportional detector response to the known amount of reference component. The reference component may be any halogenated gas phase component, and should be introduced at an injected mass proportional to that found in the samples. The reference component may contain the same halogen as the analytes. Furthermore, it may be one of the analytes targeted for measurement in the process samples. This procedure cancels most of the quantitative drift contributions related to sample pressure, temperature, and detector output.

An additional limitation of some halogen selective detectors is response linearity (detector output as a function of concentration). For example, if it is found that a component of interest does not have a perfectly linear response over a desired range of concentration, the quantitative analysis may benefit from use of a multipoint calibration rather than merely a single point calibration. Several points of calibration along the concentration axis allows use of quadratic or other exponential curve fitting procedures to relate concentration to detector response and thereby improve analytical accuracy. The invention incorporates automated multi-point component calibration, where required. This procedure uses either a switching valve to sequentially introduce standards from separate gas bottles, a gas permeation or effusion device (where various levels of concentration can be produced by diffusion or effusion of a standard mixture across permeable membranes or an orifice; these calibrators are available from multiple commercial sources such as KIN-TEK Analytical Inc.), or a mass flow controlled apparatus where flow rates for a high-level standard and a diluent can be varied over a desired range to accurately produce standard gases. For example, when using the current invention four points of calibration is routine, at the nominal 0.05, 0.50, 2.00, and 5.00 ppm levels for each component, for EO commonly, MC, VC, EC, AC, and EDC. In the case where other halogenated reaction products are being observed and measured, it is common practice to use the nearest target neighbor as a surrogate standard. This is a valid assumption since the detector response is based on molar halogen, and to the relative exclusion of other elements.

The result of the invention is to significantly improve the detection limits, the precision of measurement, and absence of chemical interferences for traditional organohalide target compounds (MC, VC, EC, AC, EDC in the EO production example). Improvements in the quality of target component measurements produces a commensurate improvement in the total effective halide TEX, or TEC (and Q, IFactor, and CCF) in the case of where organochlorides are used as modifiers.

The traditional process control parameters (Q, IFactor, CCF) represent the ratio of the total effective chlorides (TEC) being added to the catalyst and the chlorides being stripped away from the catalyst. This invention creates an alternative route to calculate these control parameters where the halide being stripped from the catalyst is measured directly in the outlet stream rather than being calculated using external hydrocarbon data and associated assumptions. Therefore, we introduce the terms K and D as new KPI reactor control parameters (or the inverse thereof), where in the case of chloride modifiers:

Total molar chlorides=TMC=[MC]+[VC]+[EC]+[AC]+[EDC]

$K$=[total molar chlorides]$_{out}$/[total molar chlorides]$_{in}$ $D$=[total molar chlorides]$_{in}$−[total molar chlorides]$_{out}$.

Both K and D are derived directly from the measurement data of the current invention without assumption as to other hydrocarbon stripping processes.

Both K and D can be adjusted using empirical effectiveness factors for catalyst modification as is current practice for deriving Q, IFactor, or CCF resulting in K' and D' using the following:

Total effective chlorides=TEC=[MC]/3+[VC]+[EC]+[AC]/6+2[EDC]

The adjustment coefficients for modification effectiveness shown are typical of values currently used, but can be any properly determined value with respect to the current invention. The adjusted total effective chloride values can then be used in an analogous fashion to derive as new KPI parameters (or the inverse thereof), where in the case of chloride modifiers:

$K'$=[total effective chlorides]$_{out}$/[total effective chlorides]$_{in}$ $D'$=[total effective chlorides]$_{in}$−[total effective chlorides]$_{out}$.

The ability to measure all halogenated modifier components in both the inlet and outlet streams forms the basis for new KPI parameters directed at the predictive ability to adjust modifier levels as a function of reactor temperature changes. It is well known that the temperature for reaction, and optimal selectivity, must be increased as a function of catalyst age. As discussed previously, this change in optimal modifier concentration as a function of reactor temperature is currently addressed either through existing algorithms or through empirical process changes used to locate new optimized modifier levels.

In the case of the EO process, using the current invention, total molar chlorides (TMC) on the inlet and outlet sample streams can be calculated from measured concentrations as:

[TMC]=[MC]+[VC]+[EC]+[AC]+[EDC]+Σ[non-targeted chlorides]

Using complete halogenated component data an equilibrium expression follows where:

$K_{eq}$=[TMC]$_{out}$/[TMC]$_{in}$

Without being bounded by theory, the Van't Hoff equation can be used to relate changes in equilibrium as a function of temperature change, where:

$\ln(K_{eq,T1}/K_{eq,T2})=\Delta H^0/R(1/T_2-1/T_1)$

Therefore, an adjusted value for $K_{eq, T2}$ at temperature $T_2$ can be calculated as:

$-\ln K_{eq,T2}=\Delta H^0/R(1/T_2-1/T_1)-\ln K_{eq,T1}$

Where $\Delta H^0$=enthalpy of reaction; $T_1$=a first reactor temperature at a first time; $T_2$=a second reactor temperature at a second time; R=molar gas constant; $K_{eq}$=[TMC$_{out}$]/[TMC$_{in}$].

The preceding is valid where the temperature range ($T_2$-$T_1$) is small enough so that →$H^0$ is constant. When this condition is not met, there are numerous methods to generalize the Van't Hoff equation to consider the temperature dependence of $\Delta H^0$. We recognize these methods and incorporate them into the current method invention.

While we describe here the use of molar quantities of modifier, the same treatment of data can be used where effectiveness coefficients are used to adjust molar concentrations for individual modifier species.

The use of complete halogenated modifier analyses to model and adjust for reactor temperature change can also be understood using Langmuir isotherm theory relating variations in catalyst surface coverage to temperature and pressure changes. It is shown experimentally that for a constant surface coverage, increases in temperature (T) require increases in partial pressure of the adsorbate (organohalide or halide). This is summarized in FIG. 1 which shows coverage (Θ) versus partial pressure of adsorbate ([TMC] under ideal gas conditions). Since each curve is data at a fixed temperature the plots are referred to as isotherms.

The Clausius-Clapeyon equation relates coverage to the change in partial pressure required for changes in temperature and can be used for determination of enthalpies of adsorption:

$(\partial \ln P/\partial 1/T)_{const\ \Theta}=\Delta H_{abs}/R$

Where, P=partial pressure of adsorbate (modifier); Θ=fraction surface coverage.

Theta (Θ) represents coverage, where at the maximum (saturation) surface coverage for a given adsorbate Θ=1. Assume in FIG. 1, for instance, where a constant theta objective (horizontal line projection) is 0.3, that this fractional coverage represents that required to maintain optimum catalyst selectivity. The model thus provides a useful tool on an operating basis to maintain optimum selectivity through modest temperature changes and cumulative catalyst production for the charge. While this theory does not encompass subsurface migration, it can be considered part of this model since certain surface coverage must be maintained to yield any requisite subsurface population of halide.

Figure 2:
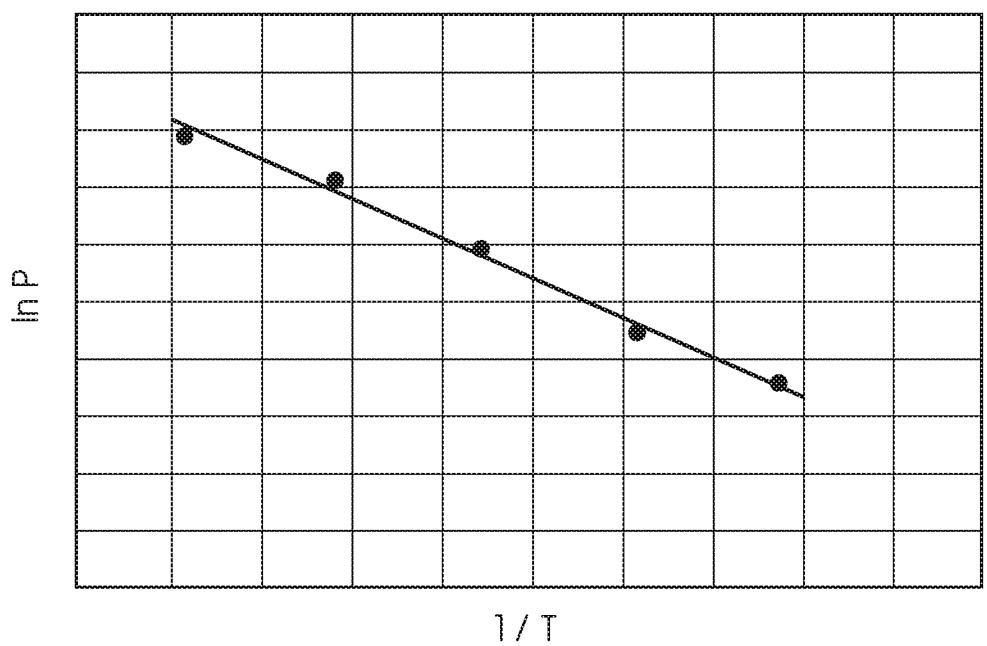
FIG. 2 shows a plot of ln P as a function of 1/T where, each point is the intersect of adsorption isotherms at constant coverage as described in FIG. 1. The linear relationship is based on Clausius-Clapeyron expression describing transitions between a gas phase and a condensed phase. The approximate linear relationship provides a useful tool as a predictive means for adjusting the partial pressures of catalyst modifying agents as a function of temperature. The slope of this line is $\Delta H_{abs}/R$ provided $\Delta H_{abs}$ remains constant over the temperature range considered. When the plot of ln P as a function of 1/T is not linear, a correction for changes in $\Delta H_{abs}$ should be applied as described within. A similar relationship is derived from chemical equilibrium theory.

Therefore, in consideration of both equilibrium and adsorption isotherm models we arrive at the same relationship since adsorption is an equilibrium process. FIG. 2 is a PT plot of ln P (partial pressure of organohalide) vs 1/T where the slope is $\Delta H_{abs}/R$. Note that the same plot type for the equilibrium model of ln $K_{eq}$ vs 1/T produces the same relationship where the slope is $-\Delta H^0/R$. Either method can be used as a predictive means for ongoing organohalide changes required as a function of reactor temperature changes to keep product selectivity optimized. We do not wish to be bound to the method of data treatment since several other methods may also produce acceptable results. The present invention uses a reactor modifier control method where both reactor inlet and reactor outlet halide analyses can be used in combination to model catalyst modifier requirements for optimal reaction selectivity.

Considering the survey nature of the present method invention, another set of KPI parameters may be derived, namely the identification and trend analysis for reactor performance based halogenated marker compounds Since weakly bound (physisorbed) modifier is likely bound to the catalyst surface, and when near an active site on the catalyst, may be part of a thermodynamic transition state leading to product formation, it can be assumed that various adducts formed from the modifier may be indicative of conditions relating to which oxidative products are formed. Using a standardized set of chromatographic conditions, libraries of chemical structure and retention indices for common halide adducts are developed using GC/MS to support further use of these halides in process understanding. The correlation of all halide species (targeted, non-targeted, and ratios thereof) to process conditions and reactor performance is part of the invented method.

Figure 3:
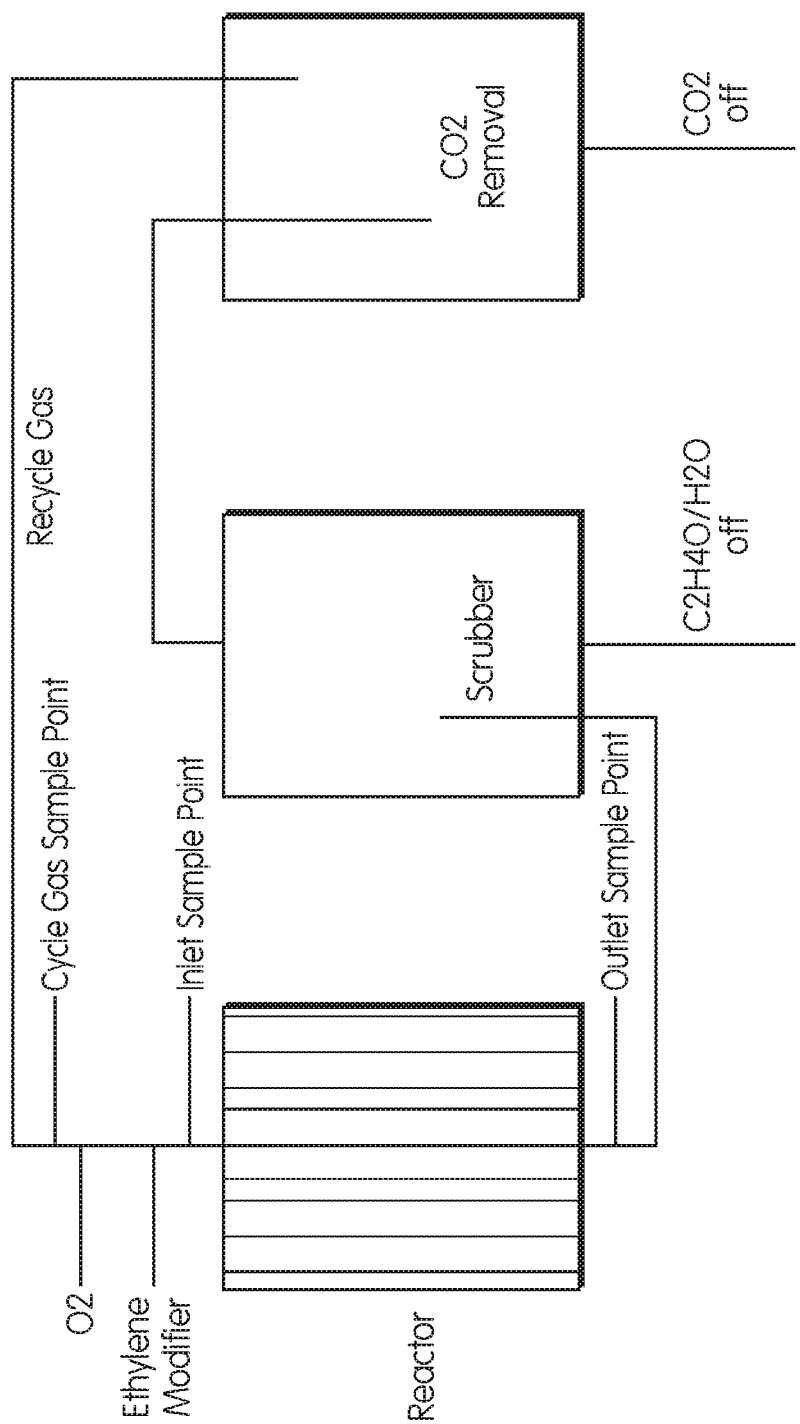
FIG. 3 shows a simplified diagram of several key sampling points in an EO plant for measurement using the current invention. We point out three key sampling points, namely, a cycle gas sample point, an inlet sample point, and an outlet sample point. Measurements made using the current invention at the reactor inlet and outlet sample points lead to either differential or ratio (equilibrium/adsorption) representation of the precise mass balance of modifier agents across the reactor catalyst bed. Measurements made using the current invention at the outlet sample point and the cycle gas sample point permit a differential expression of modifier agents lost to downstream processing units.

There are three sampling points in the EO production process where samples using this invention are commonly measured. FIG. 3 shows these as cycle gas sample point, inlet sample point, and outlet sample point. Samples at these locations have meaningful information content regarding the process. While measurements of inlet and outlet samples support halide ratio or differential expressions across the reactor, and the extended calculations described here-in, measurement of outlet and cycle gas samples permit a delta halide calculation across the downstream processing units. Since these process steps often involve aqueous systems, the delta halide in this loop provides an indication of polar halide adducts. Polar halide adducts are formed from reaction of the halides with $O_2$, the oxidation product (EO in the case of our example), other polar by-products such as aldehyde species, or $CO_2$. These adducts may be measured and tracked as KPI data and related to reactor performance.

In the case where halide speciation is not required, a total halogen or halide concentration may be measured using the invention. Rapid fraction of the organohalides from the bulk sample matrix is accomplished using the separating column, followed by backflush of the organohalide fraction directly to the halogen selective detector where response is correlated to total halogen in the sample.

Figure 4:
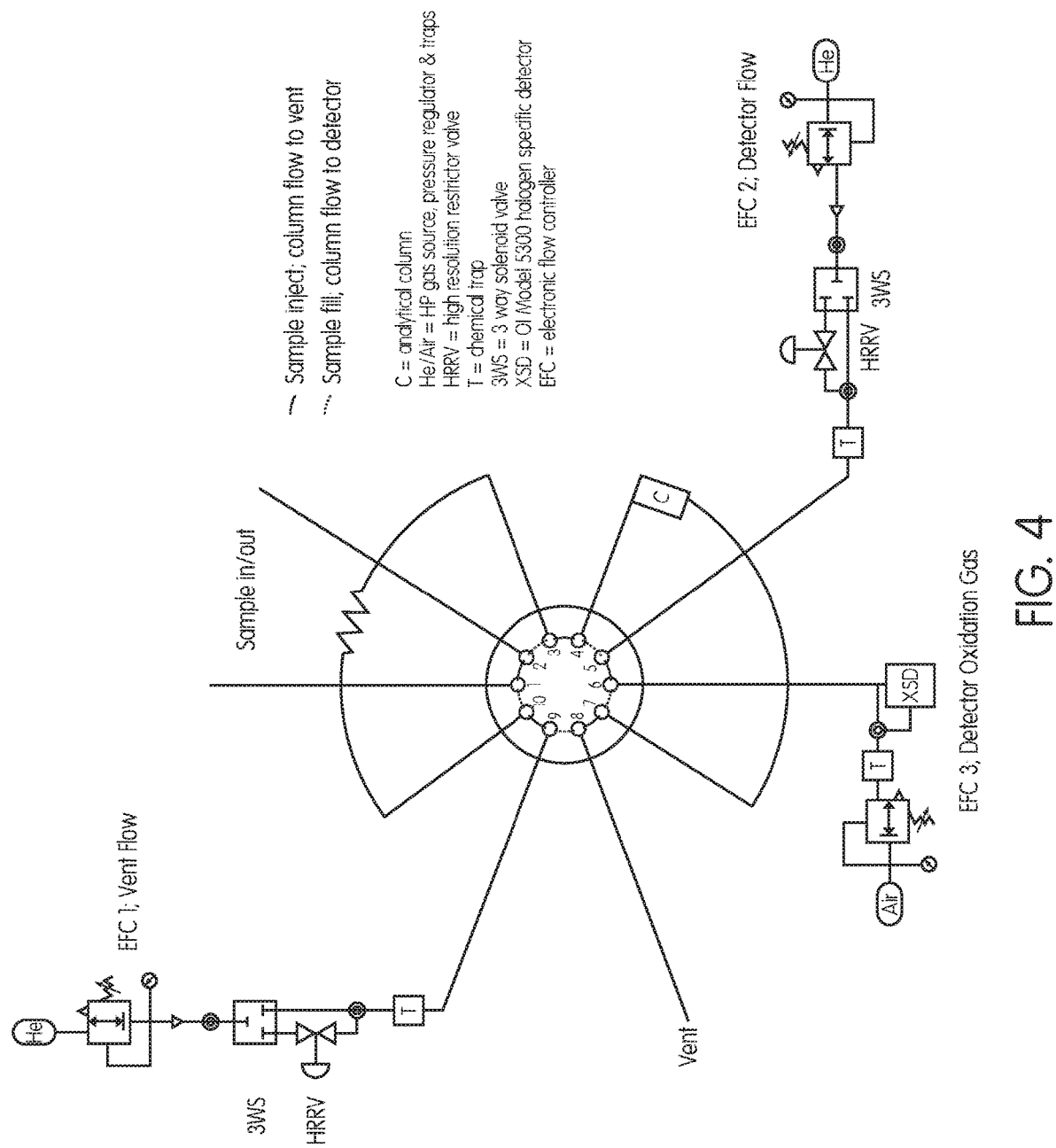
FIG. 4 shows one preferred embodiment of the invention where a single two position gas sampling valve is used to introduce sample and cut sample light ends prior to component separation and detection using a halogen selective detector.

The preferred embodiment utilizes a single packed or capillary column chosen such that halogenated components are retained preferentially, over the bulk matrix hydrocarbons and water. Optionally, a pre-column may be used to backflush any heavier chemical components if necessary prior to introduction onto the main separation column. FIG. 4 shows an example valve configuration using a single chromatographic column without backflush.

FIG. 4 shows a configuration using a single 10 port 2 position switching valve and a single separation column. In this preferred embodiment the column comprises a porous polymer packed column which is resistively heated. The use of resistive heating provides for rapid temperature programming with a wide selection of stationary phase. Three electronic mass flow controllers control gas flows in the fluidics, two for column carrier gas, and one for detector oxidation gas.

A gas sample loop is filled in one valve position and injected onto the column in the other. In the inject position the effluent from the column flows to a vent line and gas flow is regulated by EFC1 (vent flow). The fluidics remain in this position after sample injection until most of the process matrix hydrocarbons elute to vent. Prior to the elution of the halides the two position valve is switched back to the fill position where the column effluent is delivered to the halogen selective detector using EFC2 (detector flow). This process is iterated for two injections, the first injection being that of a drift correction reference gas (no process gas matrix exists in reference gas so that it may be switched back to the fill position quickly), and a second injection being that of the process gas sample. In the case where screening for inorganic halogenated components is desired, the entire sample matrix may be directed to the detector and any corrections for matrix co-elution made, if necessary.

Figure 5:
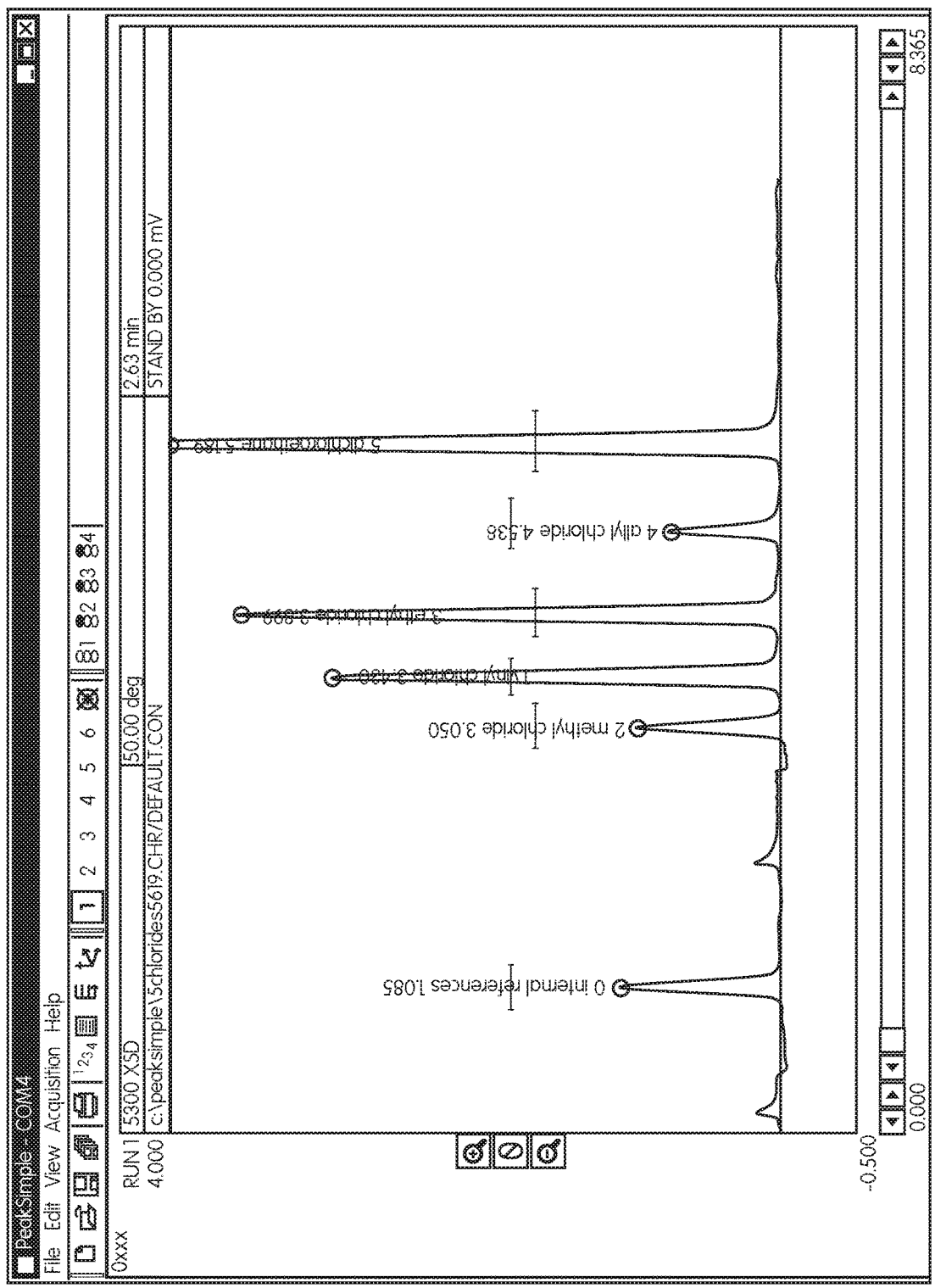
FIG. 5 is a typical chromatogram obtained using the preferred embodiment illustrating use of an internal reference drift correction component and the separation of the five process target components (MC, VC, EC, AC, and EDC) blended at 2-5 ppm in a simulated process gas background.

A typical chromatogram of the five EO process target compounds (MC, VC, EC, AC, and EDC) blended at 2-5 ppm in a simulated process gas background using this preferred embodiment is shown in FIG. 5. The chromatography shows the separation of the target species without interference from the reactor inlet process gas matrix components (ethylene, ethane, $CO_2$). The method provides for superior data quality for organohalides in terms of both sensitivity and selectivity, thereby generating more robust reactor performance metrics (TEX, or TEC in the case of organochlorides, and Q (Ifactor or CCF). The detector used is the OI Instruments XSD (Halogen Selective Detector) thermionic device (a type 2 halogen selective detector).

With the use of automated stream selection equipment and software the method is used to analyze reactor inlet and reactor outlet gas samples on an alternating basis. Since the method is a survey method (all components containing a halogen atom are detected), and since uniform response to the halogen is an attribute of type 2 halogen selective detectors, a total molar organohalide is determined for both reactor inlet and outlet samples. In this manner, an equilibrium constant ($K_{eq}=TMC_{out}/TMC_{in}$) at a given reactor temperature is computed. At catalyst startup, or at any time after startup, while keeping reactor feed constant and varying reactor temperature in small increments, $K_{eq}$ is recomputed throughout the reactor temperature changes. These data when plotted (ln $K_{eq}$ vs. 1/T) is linear with a slope of $-\Delta H_0/R$. This method provides a predictive pathway for ongoing reactor control of organohalide modifiers during reactor temperature changes during the lifetime of the catalyst.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

The invention claimed is:

1. A method for ongoing process monitoring and control of a chemical reactor in which a chemical reaction utilizing a halogenated selectivity modifier is performed, the method comprising ongoing performance of the following steps comprising:
    measuring levels of a plurality of different species of halogenated components in an inlet stream of a reactor inlet of the chemical reactor;
    measuring levels of the plurality of different species of halogenated components in an outlet stream of a reactor outlet of the chemical reactor;
    based on the measured levels of the plurality of different species of level of halogenated components at the inlet stream and the outlet stream, determining a process performance indicator comprising a halide mass balance; and
    adjusting an amount of the halogenated selectivity modifier added to the reactor, an amount of reactor feedstock, a flow rate, and/or a reactor temperature, based on the process performance indicator;

wherein the levels of a plurality of different species of halogenated components in the inlet stream and outlet stream is measured with a halogen-selective detector, wherein the halogen-selective detector comprises a gas chromatography detector.

2. The method of claim 1, wherein the plurality of different species of halogenated components in the inlet stream and the outlet stream includes all species of halogenated components contained in the inlet stream and outlet stream.

3. The method of claim 1, wherein the levels of the plurality of different species of halogenated components in the inlet stream and outlet stream is measured without significant chemical interference.

4. The method of claim 1, further comprising a separation column to separate the plurality of different species of halogenated components from the inlet stream and/or the outlet stream.

5. The method of claim 1, further comprising admitting a reference gas into the halogen-selective detector as a drift correction component.

6. The method of claim 5, wherein the reference gas comprises a halogenated component.

7. The method of claim 1, further comprising an automation system to admit a plurality of calibration gases into the halogen-selective detector to calibrate response vs. concentration.

8. The method of claim 7, wherein the automation system comprises a switching valve to introduce the plurality of calibration gases from a plurality of cylinders.

9. The method of claim 7, wherein the automation system comprises a permeation or effusion device to produce multiple level calibration gas standards in situ.

10. The method of claim 7, wherein the automation system comprises a pressure or flow controlled serial dilution system configured to produce accurate dilutions of a single master calibration gas.

11. The method of claim 1, wherein the halogen-selective detector comprises a gas or liquid phase electrolytic conductivity detector.

12. The method of claim 1, wherein the halogen-selective detector comprises an electron capture detector (ECD).

13. The method of claim 1, wherein the halogen-selective detector comprises a mass spectrometer.

14. The method of claim 1, wherein the halogen-selective detector comprises an atomic emission detector.

15. The method of claim 1, wherein the halide mass balance of the process performance indicator is based on a ratio of total molar or adjusted total molar halogen content of both reactor inlet and outlet measurements.

16. The method of claim 1, wherein the halide mass balance of the process performance indicator is based on a difference of total molar or adjusted total molar halogen content of both reactor inlet and outlet measurements.

17. The method of claim 1, further comprising:
in response to a change in temperature in the reactor to a second reactor temperature, determine an updated process performance indicator, wherein the updated process performance indicator comprises a halide mass balance based on a ratio and/or difference of total molar or adjusted total molar halogen content of both reactor inlet and outlet measurements to predict changes required in modifier levels as the reactor temperature is changed; and
adjusting the amount of the halogenated selectivity modifier added to the reactor at the second reactor temperature based on the updated process performance indicator.

18. The method of claim 1, wherein the process performance indicator comprises a process performance indicator determined based on an adsorption isotherm model to predict a required partial pressure of modifier required when the reactor temperature is changed.

19. The method of claim 1, wherein the process performance indicator comprises an amount or ratio of a marker compound.

20. The method of claim 1, wherein the chemical reaction comprises a selective oxidation of ethylene to form ethylene oxide (EO).

21. A system for ongoing process monitoring and control of a chemical reactor in which a chemical reaction utilizing a halogenated selectivity modifier is performed comprising:
a chemical reactor in which a chemical reaction occurs which utilizes a halogenated selectivity modifier, wherein the chemical reactor comprises:
an inlet comprising an inlet stream comprising reactants and a plurality of different species of halogenated components; and
an outlet comprising an outlet stream comprising reactants, products, and a plurality of different species of halogenated components;
a halogen-selective detector in fluid communication with the inlet stream and the outlet stream of the chemical reactor and configured for ongoing measurement of levels of the plurality of different species of halogenated components in the inlet stream and the outlet stream, wherein the levels of the plurality of different species of halogenated components in the inlet stream and outlet stream is measured with a halogen-selective detector, wherein the halogen-selective detector comprises a gas chromatography detector;
an analyzer configured for ongoing determination of a process performance indicator comprising a halide mass balance based on the levels of the plurality of different species of halogenated components in the inlet stream and outlet stream; and
a modifier input configured for ongoing adjustment of an amount of halogenated selectivity modifier added to the chemical reactor based on the process performance indicator.

22. A method for ongoing process monitoring and control of a chemical reactor in which a chemical reaction utilizing a halogenated selectivity modifier is performed, the method comprising ongoing performance of the following steps comprising:
providing an inlet and outlet reactor sample stream of the chemical reactor;
providing a gas chromatograph comprising a halogen selective detector in fluid communication with the reactor inlet or outlet stream; and
analyzing a level of each of a plurality of different species of halogenated selectivity modifier compounds in the reactor inlet and outlet streams to monitor or control modifier addition rates,
wherein the plurality of different species of halogenated selectivity modifier compounds analyzed in the reactor inlet and outlet streams comprises methyl chloride, vinyl chloride, ethyl chloride, ethylene dichloride, allyl chloride, and optionally all other organic and/or inorganic species of halogenated components contained in the inlet stream and outlet stream.

23. The method of claim 22, wherein a complete halide analysis of all species of halogenated components contained in the inlet stream and outlet stream is performed to produce halide analysis data, wherein a process performance indicator is computed based on the halide analysis data.

24. The method of claim 23, wherein a feedstock composition, a flow rate, and/or a reactor temperature are adjusted based on the halide analysis data.

25. The method of claim 22, wherein modifier addition rates are controlled based on a process performance indicator comprising an amount or ratio of a marker compound.

* * * * *

UNITED STATES PATENT AND TRADEMARK OFFICE
CERTIFICATE OF CORRECTION

PATENT NO. : 11,059,017 B2
APPLICATION NO. : 16/131620
DATED : July 13, 2021
INVENTOR(S) : James D. Buchner, Sr. et al.

Page 1 of 1

It is certified that error appears in the above-identified patent and that said Letters Patent is hereby corrected as shown below:

In the Claims

Column 14, Line 60, Claim 1, after "species of" delete "level of"

Signed and Sealed this
Fourteenth Day of December, 2021

Drew Hirshfeld
*Performing the Functions and Duties of the*
*Under Secretary of Commerce for Intellectual Property and*
*Director of the United States Patent and Trademark Office*